United States Patent [19]
Wallach et al.

[11] Patent Number: 5,512,544
[45] Date of Patent: Apr. 30, 1996

[54] PHARMACEUTICAL COMPOSITIONS COMPRISING AN ANTICYTOKINE

[75] Inventors: David Wallach, Rehovot; Dan Aderka, Holon, both of Israel; Harmut Engelmann, Munich, Germany

[73] Assignee: Yeda Research and Development Co. Ltd., Rehovot, Israel

[21] Appl. No.: 879,373

[22] Filed: May 7, 1992

Related U.S. Application Data

[63] Continuation-in-part of Ser. No. 524,263, May 16, 1990, abandoned, and Ser. No. 876,828, Apr. 30, 1992, which is a continuation of Ser. No. 243,092, Sep. 12, 1988, abandoned.

[30] Foreign Application Priority Data

| Sep. 13, 1987 | [IL] | Israel | 083878 |
| May 18, 1989 | [IL] | Israel | 090339 |
| May 7, 1991 | [IL] | Israel | 98078 |

[51] Int. Cl.$^6$ .................... A61K 38/16; A61K 38/17; C07K 14/435; C07K 14/47
[52] U.S. Cl. .................... 514/12; 514/21; 530/350
[58] Field of Search .................... 514/12, 21; 530/350

[56] References Cited

FOREIGN PATENT DOCUMENTS

| 2005051 | 6/1990 | Canada . |
| 0308378 | 9/1988 | European Pat. Off. . |
| 0393438 | 4/1990 | European Pat. Off. . |
| 0398327 | 5/1990 | European Pat. Off. . |
| 0412486 | 8/1990 | European Pat. Off. . |
| 0433900 | 12/1990 | European Pat. Off. . |
| 0526905 | 8/1992 | European Pat. Off. . |
| 2246569 | 6/1990 | United Kingdom . |
| 9207076 | 4/1992 | WIPO . |
| 9213095 | 8/1992 | WIPO . |

OTHER PUBLICATIONS

Beutler et al. "Cachectin: More Than A Tumor Necrosis Factor" New England J Med. 316(7) 379–385 1987.
Tracey et al. "Cachectin/Tumour Necrosis Factor" Lancet 1 1122–1125 1989.
Herrison's Principles of Internal Medicine pp. 1571–1575 1991.
Osband et al. "Problems in The Investigational Study & Chemical Use of Cancer Immuno Therapy" Immunol Today 11(6) 193–195 1990.
Engelmann et al J.B.C. vol. 264 No. 20 (7/89) pp. 11974–11980.
D. Aderka et al., "The Possible Role of Tumor Necrosis Factor (TNF) and its Natural Inhibitors, the Soluble–TNF Receptors, in Autoimmune Diseases", Israel Journal of Medical Sciences, vol. 28, No. 22, pp.: 126–130. 1992.
T. Kohno et al., "A second tumor necrosis factor receptor gene product can shed a naturally occurring tumor necrosis factor inhibitor", Proc. Natl. Acad. Sci., vol. 87, pp.: 8331–8335. 1990.
H. Loetscher et al., "Molecular Cloning and Expression of the Human 55kd Tumor Necrosis Factor Receptor", Cell, vol. 61, pp.: 351–359. 1990.
T. J. Schall et al., "Molecular Cloning and Expression of a Receptor for Human Tumor Necrosis Factor", Cell, vol. 61, pp.: 361–370. 1990.
Y. Nophar et al., "Soluble forms of tumor necrosis factor receptors (TNF-Rs). The cDNA for the type I TNF-R cloned using amino acid sequence data of its soluble form, encodes both the cell surface and a soluble form of the receptor", The EMBO Journal, vol. 9, No. 10, pp.: 3269–3278. 1990.
P. Seckinger et al., "Purification and biologic Characterization of a Specific Tumor Necrosis Factor α Inhibitor", The Journal of Biological Chemistry, vol. 264, No. 20, pp.: 11966–11973. 1989.
I. Olsson et al., "Isolation and characterization of a tumor necrosis factor binding protein from urine", Eur J Haematol, 1989; 42:270–275.
H. Engelmann et al., "Two Tumor Necrosis Factor–binding Proteins Purified from Human Urine", Journal of Biological Chemistry, vol. 265, No. 3, pp.: 1531–1536. 1990.
H. Engelmann et al., "A Tumor Necrosis Factor–binding Purified to Homogeneity from Human Urine Protects Cells from Tumor Necrosis Factor Toxicity", vol. 264, No. 20, pp.: 11974–11980. 1989.

Primary Examiner—Christina Y. Chan
Assistant Examiner—Nancy J. Degen
Attorney, Agent, or Firm—Browdy and Neimark

[57] ABSTRACT

Tumor Necrosis Factor Binding Proteins (TBPs) are useful in the treatment of autoimmune diseases and graft-versus-host reactions.

12 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Asp  Ser  Val  Cys  Pro  Gln  Gly  Lys  Tyr  Ile  His  Pro  Gln  Xaa  Asn  Ser
 1              5                        10                       15
```

PHARMACEUTICAL COMPOSITIONS COMPRISING AN ANTICYTOKINE

CROSS-REFERENCE TO RELATED APPLICATIONS

The present application is a continuation-in-part of U.S. Ser. No. 07/876,828 filed Apr. 30, 1992, and a continuation-in-part of U.S. Ser. No. 07/524,263 filed May 16, 1990, now abandoned. Said Ser. No. 07/876,828 is a continuation of Ser. No. 07/243,092 filed Sep. 12, 1988, now abandoned.

FIELD OF THE INVENTION

The present invention relates to the treatment of autoimmune diseases and graft-versus-host reactions with a Tumor Necrosis Factor (TNF) Binding Protein, herein designated TBP.

BACKGROUND OF THE INVENTION

Tumor Necrosis Factor (TNF) is a multifunctional cytokine involved in the protection of the organism, but when overproduced it can play a major pathogenic role in several diseases. TNF is known to be involved in inflammatory processes and to be a mediator of the damage to tissues in rheumatic diseases (Beutler, B. and Cerami, C. *NEJM* 316:379–385 (1987)) and of the damage observed in graft-versus-host reactions (Piguet, P. F. et al. *J. Exp. Med.* 166:1280–89 (1987)).

Two TNF Binding Proteins, designated TBP-I and TBP-II were described in U.S. patent application Ser. No. 07/243,092 filed Sep. 12, 1990 and 07/524,263, filed May 16, 1990, respectively, from the laboratory of the present inventors, and shown to protect cells from TNF toxicity and to interfere with the binding of TNF to cells. Later studies have shown that these two proteins are structurally related to two molecular species of the cell surface TNF receptors (TNF-R) and that, indeed, TBP-I is related to a soluble form of the TNF type I receptor, while TBP-II is related to a soluble form of the TNF type II receptor (Engelmann, H. et al. *J. Biol. Chem.* 264:11974–11980 (1989); Engelmann, H. et al. *J. Biol. Chem.* 265:1531–1536 (1990)). Like the cell surface receptors for TNF, the soluble forms of these receptors specifically bind TNF and can thus interfere with its binding to cells, functioning as physiological inhibitors of TNF activity. Although the primary function of the immune system is to protect an individual against infection by foreign invaders such as microorganisms, it may happen that the immune system attacks the individual's own tissues, leading to pathologic states known as autoimmune diseases, which are frequently associated with inflammatory processes. Examples of autoimmune diseases are rheumatoid arthritis, juvenile onset type I diabetes mellitus, systemic lupus erythematosus, thyroiditis and multiple sclerosis. Rheumatoid arthritis is a disease marked by signs and symptoms of inflammation of the joints. Systemic lupus erythematosus (SLE) is characterized by red, scaley patches on the skin, and by malfunction of the kidneys at the advanced stage of the disease, and is associated with inflammatory reactions triggered by deposition of immune complexes in blood vessels, particularly in the kidneys. Multiple sclerosis is a human illness characterized by relapsing, inflammatory conditions that can cause weakness, body tremors and, in extreme cases, paralysis, and is associated with immune system attack of the protective myelin sheath surrounding peripheral nerve cells.

TNF has been associated with inflammatory processes in systemic lupus erythematosus, rheumatoid arthritis and multiple sclerosis. In published European patent applications of the same assignee No. 398327 and 412486, it is disclosed that in SLE patients the serum levels of both TBP-I and TBP-II are significantly elevated and in correlation with the disease activity, indicating that TBP-I and TBP-II may be used as sensitive markers of the disease activity and may be useful in monitoring immune activation related to disease activity in SLE patients as well as in patients with other autoimmune diseases.

SUMMARY OF THE INVENTION

It has now been found, according to the present invention, that Tumor Necrosis Factor Binding Proteins are useful in the treatment of autoimmune diseases and graft-versus-host reactions. It is believed that the TBPs complement the physiological activity of the endogenous soluble TNF receptors, types I and II, whose formation in autoimmune diseases is suggested to constitute a safeguard mechanism against over-response to the damaging effects of TNF.

Accordingly, the present invention provides a method for the treatment of autoimmune diseases and graft-versus-host reactions in a patient, comprising administering to said patient an effective amount of Tumor Necrosis Factor Binding Protein, herein designated TBP, a salt, a functional derivative, a precursor or an active fraction thereof, or combinations of the foregoing.

DETAILED DESCRIPTION OF PREFERRED EMBODIMENTS

The TBPs for use in the method of the present invention may be obtained from natural sources, such as human urine (Engelmann, H. et al. *J. Biol. Chem.* 264:11974–11980 (1989); Engelmann, H. et al. *J. Biol. Chem.* 265:1531–1536 (1990); Olson, I. et al., *Eur. J. Haematol.* 42:270–275 (1989); Seckinger, P. et al., *J. Biol. Chem.* 264:11966–11973 (1989)) or by recombinant techniques (Nophar, Y. et al., *EMBO J.* 3269–3278 (1990); Schall, T. J. et al., *Cell* 61:361–370 (1990); Loetscher, H. et al., *Cell* 61:351–35 (1990)) and then further purified as described in the above-mentioned U.S. patent applications Ser. Nos. 07/243,092 and 07/524,263.

As used herein, the terms "TBPs" "TBP-I" and "TBP-II" refer to all TNF Binding Proteins from natural sources or obtained by recombinant DNA techniques, including but not limited to the TNF Binding Proteins I and II described in U.S. patent application Ser. Nos. 07/243,092 and 07/524,263, as well as to the soluble forms of the cell surface TNF receptors types I and II, and salts, functional derivatives, precursors and active fractions of the foregoing, these last definitions being as defined in U.S. patent application Ser. Nos. 07/243,092 and 07/524,263, the entire contents of each of which are hereby incoporated herein by reference.

In a preferred embodiment, the protein used in the method of the present invention is one having an amino acid sequence substantially corresponding to that of the soluble TNF inhibitory protein of U.S. Ser. No. 07/243,092. The TNF inhibitory protein of U.S. Ser. No. 07/243,092 includes the amino acid sequence: Asp-Ser-Val-Cys-Pro-Gln-Gly-Lys-Tyr-Ile-His-Pro-Gln-X-Asn-Ser, SEQ ID NO: 1 wherein X is an unidentified amino acid residue, said protein having the ability to interact with TNF in such a manner as to (a) inhibit the binding of TNF to a TNF receptor and (b) inhibit the cytotoxic effect of TNF. The complete amino acid sequence for this protein is set forth in Nophar, Y. et al., *EMBO J.* 3269–3278 (1990).

In another preferred embodiment, the protein used in the method of the present invention is one having an amino acid sequence substantially corresponding to that of the soluble Tumor Necrosis Factor Binding Protein-II of U.S. Ser. No. 07/524,263. Sequence information for this protein is published in Kohno, T. et al., *Proc. Natl. Acad. Sci. USA* 87:8331–8335 (1990). See also Australian patent 58976/90.

Another preferred embodiment of the protein used in the method of the present invention is one which includes an amino acid sequence substantially corresponding to that of the binding site of the cell surface TNF receptors types I and II.

The terminology "substantially corresponding to" is intended to comprehend proteins with minor changes to the sequence of the natural protein which do not affect the basic characteristics of the natural protein insofar as its ability to bind to TNF is concerned and to thereby inhibit the binding of TNF to a natural TNF receptor in situ.

The term "pharmaceutically acceptable" is meant to encompass any carrier that does not interfere with the effectiveness of the biological activity of the active ingredient and that is not toxic to the host to which it is, administered. For example, for parenteral administration, the TBP may be formulated in a unit dosage form for injection in vehicles such as saline, dextrose solution, normal serum albumin and Ringer's solution. Any mode of parenteral administration may be suitable, including intravenous, intramuscular and subcutaneous administration. Local administration may be preferred, however, if local inflammation is to be treated, e.g., local injection to treat joint inflammation in rheumatoid arthritis, or injection into the cerebrospinal fluid in multiple sclerosis. Besides the pharmaceutically acceptable carrier, the compositions of the invention will also comprise minor amounts of additives, such as stabilizers, excipients, buffers and preservatives.

The term "effective amount" refers to an amount of TBP that is sufficient to affect the course and severity of the autoimmune disease and to improve the patient's condition, leading to reduction or remission of the disease. The effective amount will depend on the route of administration, the disease to be treated and the condition of the patient, but is expected to be within the range of 1 µg–1 g/person/treatment. Determination of the level of TBP-I and TBP-II in the serum or other suitable body fluid of the patient, may help to establish a suitable dose for said patient, considering that the exogenously administered TBP may complement the endogenously formed TBP in neutralizing the TNF deleterious activity.

The invention will be illustrated by the following examples. In some of the examples, animal models of experimental autoimmune diseases are employed (Cohen, I. R. *J. Invest. Dermatol.* 85:34s–38s (1985)).

EXAMPLE 1

Treatment of Adjuvant Arthritis in Rats

Adjuvant arthritis is an experimental disease characterized by chronic inflammation of the joints, inducible in certain strains of rats by immunization with complete Freund's adjuvant or with fractions of Mycobacterium tuberculosis, and is considered to be a model of human rheumatoid arthritis (Pearson, C. M. *Arthritis Rheum.* 7:80–86 (1964)). The disease appears about 11–12 days after immunization, and is characterized by mononuclear cell infiltration of the synovia, most prominent in the small joints of the extremities, with panus formation, a process that may progress for months resulting in destruction of bones and ankylosis of joints. Lewis rats are immunized with M. tuberculosis (1 mg) in oil to induce adjuvant arthritis (Pearson, C. M. *Proc. Soc. Exp. Biol. Med.* 91:95–101 (1956)). Some days later, before or after the onset of overt clinical arthritis, the rats are inoculated subcutaneously with different doses of TBP-I or TBP-II once or daily for several days, and then scored for the development of arthritis on a scale of 0–16 as described (Holoshitz, Y. et al., *Science* 219:56–58 (1983)). Doses that inhibit the appearance or produce a partial inhibition of disease are effective doses. Optimal doses are those administered after onset of the disease that suppress the course and cause a permanent remission of the disease. Suitable doses for human patients can be calculated from these doses. The above-described experiment may readily be carried out by persons of ordinary skill in this art without undue experimentation to determine specific numbers for the optimal doses and suitable human doses.

EXAMPLE 2

Treatment of Experimental Autoimmune Encephalomyelitis (EAE) in Rats

Experimental autoimmune encephalomyelitis (EAE) is an experimental disease inducible in a variety of species: rats, guinea pigs, mice, rabbits, etc., by immunization with white matter of the central nervous system or with the basic protein of myelin or a fragment thereof. It is considered to be a model of multiple sclerosis and, similar to this neurological human disorder, EAE is an autoimmune disorder in which the immune system attacks the protective myelin sheath surrounding peripheral nerve cells. The disease is characterized clinically by acute paralysis and histologically by mononuclear cell infiltrates around blood vessels in the white matter of the central nervous system (Cohen, I. R., supra). Rats are injected with guinea-pig BP or the major encephalitogenic fragment of BP (amino acids 68–88) in a suitable adjuvant such as complete Freund's adjuvant to induce EAE. One day before inoculation and daily for ten days, the rats receive either saline (control) or different doses of TBP-I or TBP-II. The rats are observed for development of paralysis. Doses inhibiting the severity of disease are to be considered effective doses. Suitable doses for human patients can be calculated from these doses. The above-described experiment may readily be carried out by persons of ordinary skill in this art without undue experimentation to determine specific numbers for the optimal doses and suitable human doses.

EXAMPLE 3

Correlation Between Serum Levels of TBP-I and TBP-II and Anti-dsDNA Antibodies in SLE Patients The levels of TBP-I and TBP-II were determined in the sera of 38 SLE patients and 140 healthy controls by the ELISA method described in published European patent Applications No. 398327 and 412486. The serum concentrations (mean±SD) of TBP-I and TBP-II in the control group were 0.77±0.19 ng/ml and 3.02±0.57 ng/ml, respectively. These values were independent of age and sex. In the SLE patients, significantly higher Concentrations of TBP-I and TBP-II were observed. The mean ±SD concentrations were for TBP-I 1.89±0.89 ng/ml and for TBP-II 7.25±3.89 ng/ml.

The results were compared to the levels of anti-dsDNA antibodies, a parameter considered as a reliable and sensitive indicator of the SLE disease activity. Close examination of the extent of the correlation of the TBPs with the anti-dsDNA antibodies in individual patients revealed 3 distinctive subgroups of patients, as shown in Table 1:

Group 1—Patients with normal levels of anti-dsDNA antibodies and normal concentrations of TBP-I (9 patients) or TBP-II (11 patients).

Group 2—Patients with normal levels of anti-dsDNA antibodies but elevated concentrations of TBP-I (18 patients) or TBP-II (16 patients).

Group 3—Patients with elevation of all three parameters (11 patients).

Although both groups 2 and 3 exhibited increased TBP levels, they differed significantly not only by the extent of increase in antibodies to dsDNA, but also in other parameters of disease activity (Table I). Compared to group 2, group 3 had higher mean disease index (1.7±0.6 vs 2.4±0.8, $p<0.02$), lower complement C4 levels (9.4±4 vs 30±13 mg/dl, $p<0.001$) and a higher mean prednisone intake (20.7±17.7 vs 9±9 mg/day, $p<0.05$).

The enhanced formation of TBP-I and TBP-II, which correspond to the soluble TNF receptors type I and type II, respectively, may constitute an antagonistic mechanism of the organism to antagonize the TNF's damaging effects in the autoimmune diseases. The detection of a sub-group of SLE patients in this study, in which there is significant elevation of the TBPs, yet only marginal increase in disease activity, is consistent with the notion that the TBPs can attenuate progression of this disease and an indication that the TBPs can be used as therapeutic agents in SLE.

EXAMPLE 4

Bioactivity of TBPs in the Sera of SLE Patients—Inhibition of TNF Cytotoxicity In order to evaluate the bioactivity of the serum TBPs, serum samples were tested by a TNF cytotoxicity assay. The cytocidal activity of TNF was determined using murine A9 cells as targets. The cells were seeded in 96-well microplates at a density of 20,000 cells/well. After 24 hours, the supernatants were decanted. The cells were placed on ice and rhuTNF (5 units/ml, $6 \times 10^7$ units/mg protein) was applied alone or together with serum samples with or without added antibodies to the TBPs (described in published European patent applications 398327 and 412486) or with samples of purified TBPs isolated from human urine. After additional incubation on ice for 90 minutes, the samples were decanted and the plates rinsed twice with cold medium at this was followed by addition of Dulbecco's Modified Eagle's Minimal Essential Medium (DMEM) containing 10% fetal calf serum and 25 mg/ml cycloheximide. Cell viability was determined 12 hours later by the neutral red uptake assay.

Serum examples of SLE patients were tested by the above assay and were shown to protect A9 cells from the cytocidal effect of TNF. The extent of inhibition correlated with that observed upon application of the purified TBPs from urine in amounts identical to those present in the sera. Rabbit antisera to the TBPs, which by themselves had no effect on the A9 cytotoxicity assay, blocked the inhibitory effect of the human sera on this assay, thus confirming the assumption that the inhibition of TNF bioactivity observed, was solely due to the bioactivity of the TBPs present in the sera. This indicates that the TBPs may be effective in neutralizing the bioactivity of TBF in vivo, being capable of protecting patients from damages caused by TNF in autoimmune diseases.

TABLE 1

| GROUP | 1 | 2 | 3 |
|---|---|---|---|
| TBP | Normal Range | High | High |
| Anti-dsDNA Ab | Normal Range | Normal Range | High |
| TBP-I | | | |
| No. of Patients | 9 | 18 | 11 |
| TBP-I (ng/ml) | 0.94 ± 0.14 | 2.15 ± 0.89 | 2.17 ± 0.86 |
| Anti-dsDNA Ab % | 10.2 ± 6.62 | 5.58 ± 6.04 | 53 ± 25 |
| Disease Index | 1.33 ± 0.5 | 1.64 ± 0.6 | 2.42 ± 0.82 |
| Prednison intake (mg/day) | 0 | 9 ± 9 | 20.7 ± 17.9 |
| Complement C3 | — | 126 ± 34 | 67 ± 36 |
| Complement C4 | — | 30 ± 13.2 | 9 ± 4.6 |
| TBP-II | | | |
| No. of Patients | 11 | 16 | 11 |
| TBP-II (ng/ml) | 3.54 ± 0.75 | 8.06 ± 1.98 | 8.57 ± 2.61 |
| Anti-dsDNA Ab % | 10.2 ± 7 | 5.3 ± 5.9 | 51 ± 25 |
| Disease Index | 1.18 ± 0.4 | 1.78 ± 0.57 | 2.41 ± 0.79 |
| Prednison intake (mg/day) | 0 | 7.6 ± 9.5 | 20.7 ± 18.8 |
| Complement C3 | — | 124.8 ± 32 | 67 ± 36 |
| Complement C4 | — | 32.5 ± 12.6 | 9 ± 4 |

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or Phraseology of the present specification is to be interpreted by the skilled artisan in light of the teachings and guidance Presented herein.

It is claimed:

1. A method for the treatment of an autoimmune disease or graft-versus-host reaction in a patient, comprising administering to said patient an effective amount of at least one protein selected from the group consisting of proteins having an amino acid sequence substantially corresponding to that of the binding site of the cell surface TNF receptors types I and II and that have the same ability to bind to TNF as natural or recombinant Tumor Necrosis Factor Binding Protein I (TBP-I) or Tumor Necrosis Factor Binding Protein II (TBP-II).

2. A method according to claim 1, wherein said protein is TBP-I, TBP-II or combinations thereof.

3. A method according to claim 1, wherein said protein is a protein substantially corresponding to natural TBP-I.

4. A method according to claim 1, wherein said protein is a protein substantially corresponding to recombinant TBP-I.

5. A method according to claim 1, wherein said protein is a protein substantially corresponding to natural TBP-II.

6. A method according to claim 1, wherein said protein is protein substantially corresponding to recombinant TBP-II.

7. A method according to claim 1, wherein said protein is a combination of a protein substantially corresponding to TBP-I and a protein substantially corresponding to TBP-II.

8. A method according to claim 1 for the treatment of rheumatoid arthritis.

9. A method according to claim 1 for the treatment of systemic lupus erythematosus.

10. A method according to claim 1 for the treatment of multiple sclerosis.

11. A method according to claim 1 for the treatment of graft-versus-host reactions.

12. A method for the treatment of an autoimmune disease or graft-versus-host reaction in a patient, comprising administering to said patient an effective amount of at least one protein selected from the group consisting of proteins having an amino acid sequence substantially corresponding to that of natural or recombinant and that have the same ability to bind to TNF as natural or recombinant TBP-I or TBP-II.

\* \* \* \* \*

UNITED STATES PATENT AND TRADEMARK OFFICE
CERTIFICATE OF CORRECTION

PATENT NO. : 5,512,544
DATED : April 30, 1996
INVENTOR(S) : D. WALLACH et al.

It is certified that error appears in the above-indentified patent and that said Letters Patent is hereby corrected as shown below:

Claim 12, column 8, line 35, after "recombinant" insert
--Tumor Necrosis Factor Binding Protein I (TBP-I) or
Tumor Necrosis Factor Binding Protein II (TBP-II)--.

Signed and Sealed this

Nineteenth Day of November, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO.   : 5,512,544
DATED        : April 30, 1996
INVENTOR(S)  : D. WALLACH et al.

It is certified that error appears in the above-indentified patent and that said Letters Patent is hereby corrected as shown below:

Column 6, line 4, change "TBF" to --TNF--.

Signed and Sealed this

Twenty-fourth Day of June, 1997

Attest:

BRUCE LEHMAN

Attesting Officer                Commissioner of Patents and Trademarks